United States Patent [19]

Yokota et al.

[11] Patent Number: 4,814,514

[45] Date of Patent: Mar. 21, 1989

[54] SURFACE ACTIVE COMPOUNDS HAVING A POLYMERIZABLE MOIETY

[75] Inventors: Kinya Yokota, Shiga; Akinobu Ichihara, Kameoka, both of Japan

[73] Assignee: Dai-Ichi Kogyo Seiyaku Co., Ltd., Kyoto, Japan

[21] Appl. No.: 46,353

[22] Filed: May 6, 1987

[30] Foreign Application Priority Data

| | | |
|---|---|---|
| May 7, 1986 [JP] | Japan | 61-105119 |
| May 22, 1986 [JP] | Japan | 61-118956 |
| May 26, 1986 [JP] | Japan | 61-121954 |
| May 28, 1986 [JP] | Japan | 61-124305 |
| May 30, 1986 [JP] | Japan | 61-127006 |

[51] Int. Cl.$^4$ .................... C07C 43/11; C07C 43/215
[52] U.S. Cl. .................... 568/608; 568/609; 568/616; 568/654; 568/615; 558/31; 558/33; 558/34; 558/186; 252/351
[58] Field of Search ............ 568/616, 608, 609, 654, 568/675

[56] References Cited

U.S. PATENT DOCUMENTS

| | | | |
|---|---|---|---|
| 4,338,239 | 7/1982 | Dammann | 568/616 |
| 4,500,693 | 2/1985 | Takehara et al. | 826/333 |

FOREIGN PATENT DOCUMENTS 1484723  6/1967  France .................... 568/616

*Primary Examiner*—Howard T. Mars
*Attorney, Agent, or Firm*—Millen & White

[57] ABSTRACT

Novel surfactants of the formula:

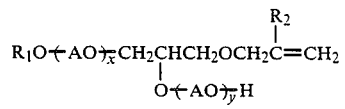

wherein
$R_1$ is alkyl, alkenyl, alkylaryl or aralkylaryl of 8–30 carbon atoms,
A is alkylene of 2–4 carbon atoms,
x is 0, or 1–100 and
y is 1–200. Sulfates, phosphates and sulfosuccinates thereof are also useful as anionic surfactants.

8 Claims, No Drawings

SURFACE ACTIVE COMPOUNDS HAVING A POLYMERIZABLE MOIETY

BACKGROUND OF THE INVENTION

This invention relates to novel surface active compounds having a polymerizable allyl or methallyl group which are particularly useful as an emulsifier in the emulsion or suspension polymerization of various monomers to produce an aqueous suspension of polymer particles.

A variety of surfactants having emulsifying, dispersing, detergent, wetting, foaming and other properties have been used in various products including textile materials, rubber and plastic products, pesticides, metals, paints, pigments, construction materials and the like while utilizing such properties. Recently, active efforts have been made to obtain better acceptance of such products among end users by using a suitable surfactant. As a result of such activities, certain defects associated with the use of conventional surfactant have be revealed.

For instance, the use of certain surfactants is indispensable for the manufacture, stabilizing or workability of paints, printing inks, adhesives and the like. After these products have been used in painting, printing, bonding or other applications, not only is the presence of such surfactants not necessary but often adversely affects the water resistance, oil resistance or other properties of the resultant films or layers. As a countermeasure of these problems, various approaches have been studied including the reduction of the quantity of surfactant or the use of a surfactant having a large molecular weight. However, they are not compatible with the storage stability and/or workability of products to be imparted by the surfactant.

Surfactants are used in the emulsion- or suspension polymerization of monomers for the production of water-based polymer emulsions or suspensions. Examples of surfactants which have been used today for such application include anionic surfactants such as alkyl sulfates, alkylbenzenesulfonates, dialkylsulfosuccinates and polyoxyalkylene alkyl (or aryl) ether sulfates; and nonionic surfactants such as polyoxyalkylene alkyl (or aryl) ethers, polyoxyethylenepolyoxypropylene block copolymers and polyoxyethylenesorbitan fatty acid esters. These surfactants may be used either singly or in combination. However, polymer emulsions and films formed therefrom including these conventional surfactants are far from complete satisfaction with respect to emulsion stabilities and film properties. Thus, many problems still remain unsolved including the polymerization, mechanical, chemical, freeze and storage stabilities and the pigment dispersing property of resultant polymer emulsions incorporating conventional emulsifiers. When films are formed from these polymer emulsions, the water resistance and adhesion thereof are often impaired by the presence of unbound surfactants in the films. When these emulsions are destroyed by means of, for example, salting out to recover polymer particles therefrom, a large amount of waste liquid containing the surfactant are necessarily formed as a by-product. For environmental reasons, this liquid must be subjected to expensive and complicated on-site water-treating processes before it can be disposed as effluent.

A number of patent documents discloses a novel type of surfactants which are polymerizable, degradable or otherwise reactive during or after use so as to be free from the foregoing defects. Examples of Japanese patent documents describing reactive anionic surfactants are listed as follows: Patent Application Nos. 46-12472, 46-34894, 49-46291, 56-29657, and Laid Open Application 51-30285, 54-14431, and 56-127697. Examples of Japanese patent documents describing reactive nonionic surfactants include Laid Open Applications Nos. 50-98484 and 56-28208.

Such reactive surfactants are mainly used in the emulsion polymerization of various monomers but they are not fully satisfactory in the practical application for such uses. One reason therefor is the fact that they are too expensive due to low yields or expensive starting materials. Another reason is that their properties such as emulsifying and dispersing capacities are less than those of conventional surfactants. Finally, despite the presence of a polymerizable moiety, they are not fully suited for such uses.

SUMMARY OF THE INVENTION

It is an object of this invention to provide new surfactant compounds having a polymerizable moiety which are free from the foregoing defects.

Other objects and advantages of this invention will become apparent to those skilled in the art upon further study of the specification and appended claims.

According to this invention, these objects have been achieved by providing compounds of the formula:

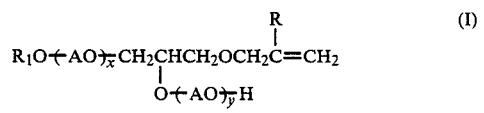

(I)

wherein $R_1$ is alkyl, alkenyl, alkylaryl or aralkylaryl of 8–30 carbon atoms, $R_2$ is hydrogen or methyl, A is alkylene of 2–4 carbon atoms, x is 0, or 1–100, and y is 1–200.

The present invention also provides anionic surfactant compounds derived from compounds of the formula (I). They are sulfates, phosphates and sulfosuccinates of the formulae, respectively

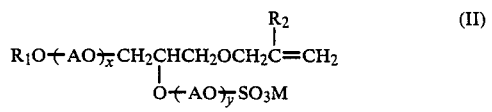

(II)

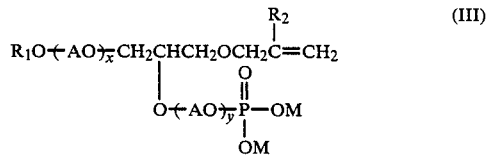

(III)

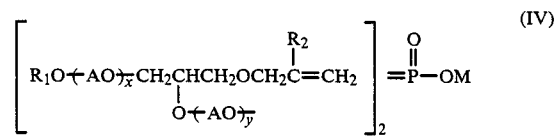

(IV)

-continued

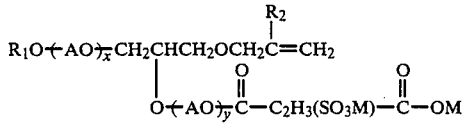 (V)

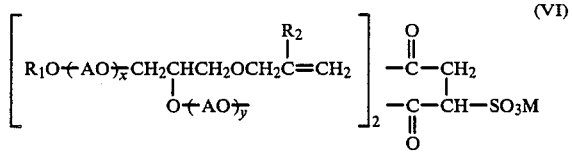 (VI)

wherein M is hydrogen, alkali metal, $NH_4$ or lower alkanolamine, and other symbols are as defined above.

DETAILED DISCUSSION

The compounds of this invention of the above formula (I) may be prepared by reacting a compound of the formula:

$$R_1O(AO)_xH \quad (VII)$$

first with a glycidyl ether of the formula:

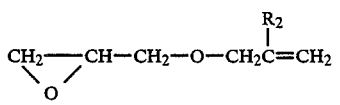 (VIII)

and then with an alkylene oxide of 2-4 carbon atoms.

Examples of starting compounds of the formula (VII) (for x=0) includes alkyl alcohols of 8-30 carbon atoms such as octyl alcohol, nonyl alcohol, decyl alcohol, undecyl alcohol, lauryl alcohol, tridecyl alcohol, myristyl alcohol, pentadecyl alcohol, palmityl alcohol, heptadecyl alcohol, stearyl alcohol, nonadecyl alcohol and eicocyl alcohol; alkenyl alcohols of the same carbon atom range such as octenyl alcohol, nonenyl alcohol, decenyl alcohol, undecenyl alcohol, dodecenyl alcohol, tridecenyl alcohol, tetradecenyl alcohol, pentadecenyl alcohol, hexadecenyl alcohol, heptadecenyl alcohol, and oleyl alcohol; alkylphenols of the same carbon atom range such as butylphenol, dibutylphenol, sec.-butylphenol, di-sec.-butylphenol, tert.-butylphenol, octylphenol, nonylphenol, dinonylphenol, dodecylphenol and didodecylphenol; and aralkylphenols such as styrylated phenol, benzylphenol, cumylphenol, and corresponding di- or tri-substituted phenols.

Adducts of the above aliphatic alcohols or phenols with 1-100 moles, preferably 1-50 moles of ethylene oxide, propylene oxide, butylene oxide or isobutylene oxide (Formula VII, x is 1-100) may also be used.

Compounds (VII) are first reacted with allyl glycidyl ether ($R_2=H$) or methallyl glycidyl ether ($R_2=CH_3$) in the presence of a catalyst such as triethylamine, and boron trifluoride-ether complex to give compounds of the formula:

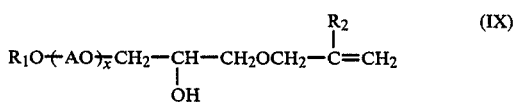 (IX)

The compounds (I) of this invention are produced by the addition of 1-200, preferably 2-100 moles of alkylene oxide of 2-4 carbon atoms to the compounds (IX).

The reaction may be carried out in the presence of a conventional basic or acidic catalyst. The oxyalkylene moieties included in the compounds (I) may be homopolymers, block or random copolymers of straight or branched alkylene oxides of 2-4 carbon atoms. These oxyalkylene moieties must, however, contain a sufficient number of oxyethylene units to render the moieties hydrophilic when they are copolymers containing alkylene oxides of 3 or 4 carbon atoms. Moieties $R_1$ constitute hydrophobic moieties of the nonionic surfactant compounds of this invention. The allyl or methallyl group of the compounds of the formula (I) provides a polymerization site.

The nonionic surfactant compounds of the formula (I) may be converted to anionic surfactant compounds by chemically modifying the terminal hydroxyl group thereof.

One such approach includes the steps of reacting the compounds of the formula (I) with sulfuric acid or sulfamic acid and then optionally converting the resulting free sulfate esters (when sulfuric acid is used) or ammonium salts (when sulfamic acid is used) into corresponding alkali metal or alkanolamine salts such as monoethanolamine by conventional procedures whereby sulfate esters of the formula (II) are obtained.

Another approach includes the steps of reacting the compounds of formula (I) with phosphorus pentoxide or phosphorus oxychloride and then optionally converting the resulting free phosphate esters into corresponding salts with alkali metal, ammonium or alkanolamine salts whereby mixtures of mono-esters of the formula (III) and di-esters of the formula (IV) are obtained. These mixtures may be used as an anionic surfactant without being isolated into their constituents.

A further approach includes the steps of reacting the compounds of the formula (I) with maleic anhydride, reacting resultant maleate esters with an alkali metal bisulfite and then optionally converting the resulting alkali metal sulfosuccinates into corresponding free acids or ammonium or alkanolamine salts. When at least one mole of maleic anhydride is used relative one mole of the compounds of the formula (I) in the above reaction, mixtures of half ester isomers having a sulfo group $SO_3M$ attached to either alpha or beta position relative to the terminal carboxyl group in the formula (V) are obtained. These mixtures may also be used as an anionic surfactant without isolation. Conversely, when at least two moles of the compounds of the formula (I) are reacted with one mole of maleic anhydride, di-esters of the formula (VI) are obtained.

The new surfactant compounds of this invention can meet a user's demand for a reactive surfactant which no longer functions as a surfactant immediately after it has played a desired role in the manufacture, storage or processing of various products such as paints, printing inks and adhesives. These compounds may be rendered inactive after use by incorporating a suitable polymerization initiator to the formulations containing the same prior to coating, printing, bonding or other application steps and/or by curing the compounds with heat or UV rays.

The surfactants of this invention are particularly useful as an emulsifier in the emulsion or dispersion polymerization of ethylenically unsaturated monomers. Examples of monomers include acrylic monomers such as acrylic acid, methyl acrylate, butyl acrylate, 2-ethylhexyl acrylate, methyl methacrylate, acrylonitrile, acrylamide and 2-hydroxyethyl acrylate; aromatic monomers such as styrene and divinylbenzene; vinyl esters such as vinyl acetate; halogen-containing monomers such as vinyl chloride and vinylidene chloride; conjugated diene monomers such as butadiene, isoprene and chloroprene; ethylene, maleic anhydride and methyl maleate.

Any known initiator such as hydrogen peroxide, potassium persulfate, azobisisobutyronitrile and benzoyl peroxide may be used in the emulsion polymerization in combination with a known polymerization promoter such as sodium bisulfite and ammonium ferrous sulfate.

The surfactants of this invention may be used in an amount of 0.1 to 20%, preferably 0.2 to 5.0% by weight of the total monomers singly or in combination with a conventional emulsifiers or protective colloid.

The resulting polymer emulsions or dispersions may be applied to woods, metals, paper, textiles and concrete structures as an adhesive, coating agent or reinforcing agent.

The new surfactant compounds of this invention find use not only as an emulsifier or dispersant of various materials such as monomers in the emulsion or suspension polymerization, waxes, dyes, pigments and pesticides, but also as post-treating agents for textile materials and anti-static agents for plastic products. By the use of the surfactants of this invention, defects of conventional surfactants remaining after use may be alleviated.

The invention is further illustrated by the following examples, in which all parts and percentages are by weight.

EXAMPLE 1

A reactor equipped with a stirrer, thermometer and reflux condenser was charged with 220 g (1.0 mol) of nonylphenol and 1.5 g of triethylamine as a catalyst. 114 g (1.0 mol) of allyl glycidyl ether was added dropwise. The mixture was heated at 100° C. for 5 hours with stirring.

The reaction product was transferred to an autoclave and reacted with 10, 30 or 100 moles of ethylene oxide in the presence of potassium hydroxide catalyst at 130° C. at a pressure of 1.5 kg/cm$^2$. Surfactants No. 1 (10 moles of EO), No. 2 (30 moles of EO) and No. 3 (100 moles of EO) were obtained.

EXAMPLE 2

The reactor as used in Example 1 was charged with 186 g (1.0 mol) of lauryl alcohol and 0.6 g of boron trifluoridether complex. 114 g (1.0 mol) of allyl glycidyl ether was added dropwise. The mixture was heated at 80° C. for 5 hours with stirring.

The reaction product was transferred to an autoclave and reacted with 5, 20 or 50 moles of ethylene oxide analogously to Example 1. Surfactants No. 4 (5 moles of EO), No. 5 (20 moles of EO) and No. 6 (50 moles of EO) were obtained.

EXAMPLE 3

The reactor as used in Example 1 was charged with 856 g (1.0 mol) of distyrylated phenol/ethylene oxide (10 mol)/propylene oxide (2 mol) block adduct and 2 g of boron trifluoride-ether complex. 114 g (1.0 mol) of allyl glycidyl ether was added dropwise. The mixture was heated at 80° C. for 5 hours with stirring.

The reaction product was transferred to an autoclave and reacted with 15 or 40 moles of ethylene oxide analogously to Example 1. Surfactants No. 7 (15 moles of EO) and No. 8 (40 moles of EO) were obtained.

EXAMPLE 4

The reactor as used in Example 1 was charged with 1588 g (1.0 mol) of oleyl alcohol/ethylene oxide (30 mol) adduct and 3 g of boron trifluoride. 114 g (1.0 mol) of allyl glycidyl ether was added dropwise. The mixture was heated at 80° C. for 5 hours with stirring.

The reaction product was transferred to an autoclave and reacted with 40 moles of ethylene oxide and 10 moles of propylene oxide at random analogously to Example 1 to obtain surfactant No. 9.

EXAMPLE 5

The reactor as used in Example 1 was charged with 385 g (1.0 mol) of stearyl alcohol/propylene oxide (2 mol) adduct and 1.5 g of boron trifluoride-ether complex. 114 g (1.0 mol) of allyl glycidyl ether was added dropwise. The mixture was heated at 80° C. for 5 hours with stirring.

The reaction product was transferred to an autoclave and reacted with 2 or 5 moles of ethylene oxide analogously to Example 1. Surfactants No. 10 (2 moles of EO) and No. 11 (5 moles of EO) were obtained.

EXAMPLE 6

The reactor as used in Example 1 was charged with 278 g (1.0 mol) of di-sec.-butylphenol/butylene oxide (2 mol) adduct and 1 g of boron trifluoride. 114 g (1.0 mol) of allyl glycidyl ether was added dropwise. The mixture was heated at 80° C. for 5 hours with stirring.

The reaction product was transferred to an autoclave and reacted with 2 moles of propylene oxide and 15 moles of ethylene oxide analogously to Example 1 to obtain surfactant No. 12.

EXAMPLE 7

The reactor as used in Example 1 was charged with 1244 g (1.0 mol) of tribenzylphenol/ethylene oxide (20 moles) adduct and 4 g of boron trifluoride-ether complex. 114 g (1.0 mol) of allyl glycidyl ether was added dropwise. The mixture was heated at 80° C. for 5 hours with stirring.

The reaction product was transferred to an autoclave and reacted with 5 moles of propylene oxide analogously to Example 1 to obtain surfactant No. 13.

EXAMPLE 8

A reactor equipped with stirrer and thermometer was charged with 387 g (0.5 mol) of surfactant No. 1 obtained in Example 1 and 58.2 g (0.6 mol) of sulfamic acid. The mixture was heated at 120° C. for 3 hours with stirring. After unreacted sulfamic acid was filtered off, ammonium salt of the sulfate of compound No. 1 was obtained.

Ammonium salts of the sulfates of surfactants Nos. 6, 7 and 12 were produced, respectively, analogously to the above procedure.

The ammonium salts of sulfate esters of surfactants Nos. 1, 6, 7 and 12 are identified as surfactants Nos. 14–17, respectively.

EXAMPLE 9

The reactor as used in Example 8 was charged with 387 g (0.5 mol) of surfactant No. 1 obtained in Example 1 and 22.7 g (0.16 mol) of phosphorus pentoxide. The mixture was heated at 80° C. for 15 hours with stirring. A mixture of mono- and di-phosphate esters in 50:50 molar ratio was obtained and identified as surfactant No. 18.

Similarly, the phosphate esters of surfactants Nos. 6, 7 and 12 were prepared and identified as surfactants Nos. 19–21, respectively. The molar ratios of mono- and di-esters in surfactants Nos. 19–21 were 58:42, 80:20 and 63:37, respectively.

EXAMPLE 10

A reactor equipped with stirrer, thermometer and condenser was charged with 387 g (0.5 mol) of surfactant No. 1 obtained in Example 1 and 24.5 g (0.25 mol) of maleic anhydride. The mixture was heated at 160° C. with stirring for 8 hours while removing formed water. After cooling to 40° C., the reaction product was reacted with 26 g (0.25 mol) of sodium bisulfite in 60 g of water and 60 g of isopropyl alcohol at 80° C. for 5 hours. The sodium salt of di-sulfosuccinate ester of surfactant No. 1 was obtained and identified as surfactant No. 22

Similarly, corresponding sulfosuccinates of surfactants Nos. 6, 7 and 12 were prepared and identified as surfactants Nos. 23–25, respectively.

EXAMPLE 11

The reactor as used in Example 10 was charged with 387 g (0.5 mol) of surfactant No. 1 obtained in Example 1 and 49 g (0.5 mol) of maleic anhydride. The mixture was heated at 80° C. for 3 hours with stirring to produce a maleic acid half ester. This product was diluted with 1400 g of water and then neutralized with 41.7 g of 48% sodium hydroxide (0.5 mol). Then 57.2 g (0.55 mol) of sodium bisulfite was added and the mixture allowed to react at 80° C. for 3 hours. The sodium salt of mono-sulfosuccinate ester of surfactant No. 1 was obtained and identified as surfactant No. 26.

Similarly, corresponding sulfosuccinates of surfactants Nos. 6, 7 and 12 were prepared and identified as surfactants Nos. 27–29, respectively.

EXAMPLE 12

The values of surface tension of the surfactants Nos. 1–29 of this invention in a 0.1% aqueous solution were measured according to the Traube's method and are shown in Table 1. Also indicated, for comparison purposes, are the measured values for a conventional surfactant of analogous structure.

TABLE 1

Surface Tension of Compounds of This Invention

| No. | $R_1$ | $R_2$ | —(AO)$_x$— | —(AO)$_y$— | Surface Tension at 0.1% at 25° C. (dyne/cm) |
|---|---|---|---|---|---|
| 1 | Nonylphenyl | H | — | EO 10 | 32.0 |
| 2 | Nonylphenyl | " | — | EO 30 | 44.0 |
| 3 | Nonylphenyl | " | — | EO 100 | 56.0 |
| 4 | Lauryl | " | — | EO 5 | 27.0 |
| 5 | Lauryl | " | — | EO 20 | 42.0 |
| 6 | Lauryl | " | — | EO 50 | 48.0 |
| 7 | Distyrylphenyl | " | EO 10, PO 2 | EO 15 | 51.0 |
| 8 | Distyrylphenyl | " | EO 10, PO 2 | EO 40 | 53.0 |
| 9 | Oleyl | " | EO 30 | PO 10, EO 40 | 60.0 |
| 10 | Stearyl | " | PO 2 | EO 2 | water insoluble |
| 11 | Stearyl | " | PO 2 | EO 5 | 32.0 |
| 12 | Di-s-butylphenyl | " | BO 2 | PO 2, EO 15 | 48.0 |
| 13 | Tribenzylphenyl | " | EO 20 | PO 5 | 46.0 |

| No. | Description | M | Surface Tension at 0.1% at 25° C. (dyne/cm) |
|---|---|---|---|
| 14 | Sulfate of No. 1 | $NH_4$ | 38.0 |
| 15 | Sulfate of No. 6 | " | 48.0 |
| 16 | Sulfate of No. 7 | " | 52.0 |
| 17 | Sulfate of No. 12 | " | 43.0 |
| 18 | Phosphate of No. 1 | H | 36.0 |
| 19 | Phosphate of No. 6 | " | 49.0 |
| 20 | Phosphate of No. 7 | " | 52.0 |
| 21 | Phosphate of No. 12 | " | 49.0 |
| 22 | Di-sulfosuccinate of No. 1 | Na | 31.0 |
| 23 | Di-sulfosuccinate of No. 6 | " | 47.0 |
| 24 | Di-sulfosuccinate of No. 7 | " | 46.0 |
| 25 | Di-sulfosuccinate of No. 12 | " | 42.0 |
| 26 | Mono-sulfosuccinate of No. 1 | Na | 36.0 |
| 27 | Mono-sulfosuccinate of No. 6 | " | 47.0 |
| 28 | Mono-sulfosuccinate of No. 7 | " | 52.0 |
| 29 | Mono-sulfosuccinate of No. 12 | " | 48.0 |
| Comp. 1 | Nonylphenol/EO 10 adduct | | 31.0 |
| Comp. 2 | Na dodecylbenzenesulfonate | | 36.0 |
| Comp. 3 | Nonylphenol/EO 8 adduct sulfate $NH_4$ salt | | 40.0 |

TABLE 1-continued

| Surface Tension of Compounds of This Invention | | |
|---|---|---|
| Comp. 4 | Na dioctylsulfosuccinate | 33.0 |

EO = Ethylene oxide,
PO = Propylene oxide,
BO = Butylene oxide

EXAMPLE 13

The dispersing and emulsifying capacities of compounds of this invention were measured using carbon black and kerosene, respectively, and are shown in Table 2. Also indicated, for comparison purposes, are those of conventional surfactants of analogous structure.

The test methods used in these experiments are as follows:

Dispersing Capacity:

Into a 100 ml measuring cylinder were placed 1 g of the surfactant of this invention and 10 g of carbon black. Water was added until a total volume of 100 ml was reached. The mixture was shaken 100 times for 1 minutes and then allowed to stand for 1 hour at 25° C. 30 ml of the dispersion were withdrawn from the cylinder and filtered through a glass filter. The residue on the filter was dried at 105° C. and weighed. The dispersing capacity was calculated by the following equation.

Dispersing Capacity (%) = Weight of Residue (g)/3 (g) × 100

Emulsifying Capacity:

Into a 100 ml measuring cylinder were placed 5 ml of 0.5% aqueous solution of the surfactant of this invention and 5 ml of kerosene. The mixture was shaken 100 times for 1 minute and allowed to stand for 1 hour at 25° C. The volume of emulsified layer was measured. The emulsifying capacity was calculated by the following equation:

Emulsifying Capacity (%) = Emulsified Layer (ml)/10 (ml) × 100

TABLE 2

| No. | Dispersing Capacity (%) | Emulsifying Capacity (%) |
|---|---|---|
| 1 | 70 | 70 |
| 14 | 80 | 80 |
| 18 | 80 | 75 |
| 22 | 75 | 60 |
| 26 | 80 | 65 |
| 7 | 75 | 65 |
| 16 | 60 | 50 |
| 20 | 80 | 50 |
| 24 | 80 | 60 |
| 28 | 60 | 60 |
| Comp. 1 | 75 | 80 |
| Comp. 2 | 85 | 30 |
| Comp. 4 | 20 | 50 |

EXAMPLE 14

5 g of a surfactant of this invention and 30 g of polyvinyl alcohol (saponification degree of 80 mole %, average viscosity polymerization degree of 1700) were dissolved in 300 g of water with stirring with warming. 240 g of vinyl acetate monomer was added dropwise and emulsion polymerized in the presence of 1 g of ammonium persulfate by the known method to prepare a polymer emulsion. To this emulsion was added 30 g of dibutyl phthalate.

The values of adhesion strength were measured and are shown in Table 3.

TABLE 3

| No. | Normal Adhesion[1] Strength (kg/cm$^2$) | Water Resistant[2] Adhesion Strength (kg/cm$^2$) |
|---|---|---|
| 6 | 185 | 90 |
| 15 | 180 | 100 |
| 19 | 160 | 90 |
| 23 | 170 | 90 |
| 27 | 170 | 80 |
| Comp. 1 | 120 | 35 |
| Comp. 2 | 92 | 10 |
| Comp. 3 | 86 | 20 |

[1]Compression/shear adhesion strength of birch/birch test piece measured by the method according to JIS-K6804.
[2]The same measurement as above after soaking in water for 3 hours at 30° C.

EXAMPLE 15

A piece of polypropylene nonwoven fabric (2.5 cm × 10 cm) was soaked in b 1% aqueous solution of the surfactant of this invention for 1 minute and air dried at 120° C. The treated fabric was suspended in a 100 ml beaker containing 50 ml of water so that only a 1 cm length of the distal end was submerged in water. After 5 minutes, the height of water-penetrated area above the liquid level was determined.

The above test was repeated for the same fabric after treating with the surfactant, drying and rinsing with tap water for 1 minutes. The results before and after the rinsing are shown in Table 4.

TABLE 4

| No. | Before Rinsing (mm) | After Rinsing (mm) |
|---|---|---|
| 12 | 11 | 8 |
| 17 | 13 | 9 |
| 21 | 9 | 7 |
| 25 | 13 | 10 |
| 29 | 12 | 10 |
| Comp. 1 | 18 | 1 |
| Octylphenol/EO 10 adduct sulfate Na | 14 | 0 |

EXAMPLE 16

Into a flask were placed 5 g of a surfactant of this invention, 50 g of methyl acrylate, 0.5 g of benzoyl peroxide and 200 g of toluene. The mixture was heated at 80° C. for 10 hours with stirring. The resulting polymer solution was cast on a glass plate to a dry film thickness of 0.5 mm and dried at room temperature for one day and then at 80° C. for 3 hours in an oven. The film was tested for appearance, water resistance and specific surface resistivity. The results are shown in Table 5.

TABLE 5

| Surfactant No. | Appearance | Water[1] Resistance | Specific[2] Surface Resistivity (ohm) |
|---|---|---|---|
| 1 | transparent | good | $1 \times 10^{12}$ |
| 14 | " | " | $1 \times 10^{11}$ |
| 18 | " | " | $1 \times 10^{10}$ |
| 22 | " | " | $1 \times 10^{11}$ |
| 26 | " | " | $1 \times 10^{12}$ |
| Octylphenol/EO 3 adduct | opaque | bad | $1 \times 10^{15}$ |
| Sorbitan monooleate | transparent | " | $1 \times 10^{13}$ |
| Glycerine monostearate | opaque | " | $1 \times 10^{12}$ |

[1]Whitening of the film was observed after soaking in water and graded according to the following schedule:
Good: not whitening for over 1 hour.
Fair: whitening between 10–60 minutes.
Bad: whitening within less than 10 minutes.
[2]Measurement was made at 25° C. at RH of 60% using TERAOHM METER Model VE-30 sold by Kawaguchi Electric Co., Ltd.

EXAMPLE 17

A solution of 5 parts of the surfactant of this invention in 295 parts of water was warmed to a temperature of 70° C. To this solution were added 20 parts of ethyl acrylate or vinyl acetate monomer and 0.5 parts of ammonium persulfate with stirring. 10 minutes after the initiation of the polymerization reaction, additional 180 parts of the monomer were added dropwise over 3 hours with stirring. Then the mixture was stirred for an additional one hour at 70° C. and allowed to cool.

A coating of resulting polymer emulsion was applied to a glass plate, dried at room temperature for 24 hours and cured at 110° C. for 3 minutes to make a film. The polymer emulsion and the film made therefrom were tested for stabilities and water resistances. The results are shown in Table 6.

(1) After polymerization, the polymer emulsion was filtered through a 150 mesh stainless steel screen. Agglomerates retained on the screen were thoroughyl washed with water and weighed. Percents of the agglomerates relative to the charged quantity of the monomer was calculated.

| Very good: | <0.5% |
|---|---|
| Good: | 0.5–2% |
| Fair: | 2–5% |
| Bad: | >5% |

(2) The emulsion was centrifuged in a Marlon type mechanical stability tester at 10 kg/cm² at 1,000 rpm for 5 minutes and then filtered through a 80 mesh stainless steel screen. Agglomerates retained on the screen were thoroughly washed with water and weighed. The percentage of the agglomerates relative to the charged quantity of the monomer was calculated and graded according to the above schedule.

(3) The polymer film formed on the glass plate was soaked in water and the whitening of the film was observed visually.

| Very Good: | No whitening at all over 1 hour. |
|---|---|
| Good: | Slightly whitened after 1 hour. |
| Fair: | Whitened between 10–30 minutes. |
| Bad: | Whitened immediately. |

EXAMPLE 18

A solution of 5 parts of a combination of surfactants listed in the Table 7 below in 295 parts of water was warmed to 80° C. To this solution were added 0.3 parts of ammonium persulfate and 20 parts of a 7:3 monomer mixture of n-butyl acrylate and styrene with stirring. 10 minutes after the initiation of the polymerization reaction, an additional 180 parts of the monomer mixture were added dropwise over 3 hours with stirring. Then the mixture was stirred for additional 1 hour at 80° C. and allowed to cool.

TABLE 6

| Surfactant No. | Monomer | Emulsion Stability (1) Polymerization | Emulsion Stability (2) Mechanical | Polymer Film Water Resistance Dried at R.T. | Polymer Film Water Resistance Dried at R.T. and cured at 110° C. |
|---|---|---|---|---|---|
| 1 | Ethyl acrylate | very good | very good | very good | very good |
| 14 | " | " | " | " | " |
| 18 | " | good | " | " | " |
| 22 | " | very good | " | " | " |
| 26 | " | " | " | " | " |
| Nonylpheno/EO 30 adduct | " | " | fair | good | good |
| Na dodecylbenzenesulfonate | " | good | bad | bad | fair |
| 1 | Vinyl acetate | very good | very good | fair | good |
| Nonylphenol/EO 20 adduct | " | good | good | bad | fair |
| Nonylphenol/EO 6 adduct sulfate NH4 | " | very good | good | bad | fair |

The resulting polymer emulsion and the films prepared therefrom were tested for stabilities and water resistances as in Example 17. The results are shown in Table 7.

TABLE 7

| Surfactant combination | | Emulsion Stability Polymerization | Emulsion Stability Mechanical | Polymer Film Water Resistance Dried at R.T. | Polymer Film Water Resistance Dried at R.T. and cured at 110° C. |
|---|---|---|---|---|---|
| No. 1 (70%) | Na dodecylbenzene- | very good | very good | fair | good |

TABLE 7-continued

| Surfactant combination | | Emulsion Stability | | Polymer Film Water Resistance | |
| --- | --- | --- | --- | --- | --- |
| | | Polymerization | Mechanical | Dried at R.T. | Dried at R.T. and cured at 110° C. |
| | sulfonate (30%) | | | | |
| No. 14 (20%) | Nonylphenol/EO 50 adduct (80%) | " | " | good | very good |
| No. 18 (20%) | Nonylphenol/EO 50 adduct (80%) | " | " | " | " |
| No. 22 (20%) | Nonylphenol/EO 50 adduct (80%) | " | good | " | " |
| No. 26 (20%) | Nonylphenol/EO 50 adduct (80%) | " | very good | " | " |
| No. 1 (70%) | No. 14 (30%) | " | " | very good | " |
| No. 1 (70%) | No. 18 (30%) | " | " | " | " |
| Nonylphenol/ EO 80 adduct (80%) | Na dodecylbenzene- sulfonate (20%) | " | fair | bad | fair |

What is claimed is:

1. A compound of the formula:

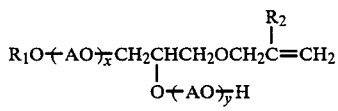

wherein $R_1$ is alkyl, alkenyl, alkylaryl or aralkylaryl of 8-30 carbon atoms, $R_2$ is hydrogen or methyl, A is alkylene of 2-4 carbon atoms, x is 0, or 1-100, and y is 1-200.

2. The compound of claim 1, wherein x is 0, y is 2-100 and A is ethylene.

3. The compound of claim 1, wherein x is 1-50, y is 2-100 and at least one of —AO— and —AO— is a polyoxyethylene chain.

4. A free alcohol compound of claim 1 of the formula set forth therein wherein at least one of —(AO)$_x$— and —(AO)$_y$— is a polyoxyethylene chain or a mixed $C_2$-$C_4$ polyoxyalkylene chain which contains a sufficient number of oxyethylene units to render the moiety hydrophilic.

5. A compound of claim 4 wherein x is 0.

6. A compound of claim 4 wherein x is 1-100.

7. A compound of claim 4 wherein x is 1-50, y is 2-200 and at least one of —(AO)$_x$ and —(AO)$_y$ is a polyoxyethylene chain.

8. A free alcohol compound of claim 1, wherein $R_1$ is nonylphenyl, lauryl, oleyl or stearyl.

* * * * *

UNITED STATES PATENT AND TRADEMARK OFFICE
CERTIFICATE OF CORRECTION

PATENT NO. : 4,814,514

DATED : March 21, 1989

INVENTOR(S) : Yokota et al

It is certified that error appears in the above-identified patent and that said Letters Patent is hereby corrected as shown below:

Column 14, Claim 3, Line 22:

Reads: "2-100 and at least one of —AO— and —AO— is a"

Should Read: --2-100 and at least one of $-(AO)_x-$ and $-(AO)_y-$ is a--

Signed and Sealed this

Twenty-eighth Day of November 1989

*Attest:*

JEFFREY M. SAMUELS

*Attesting Officer*     *Acting Commissioner of Patents and Trademarks*